United States Patent [19]

Weiss et al.

[11] Patent Number: 5,404,765

[45] Date of Patent: Apr. 11, 1995

[54] INLET VALVE FOR A HIGH-VACUUM ANALYZER WITH BYPASS EVACUATION

[75] Inventors: Gerhard Weiss; Alfred Kraffert, both of Weyhe, Germany

[73] Assignee: Bruker-Franzen Analytik GmbH, Bremen, Germany

[21] Appl. No.: 9,793

[22] Filed: Jan. 27, 1993

[30] Foreign Application Priority Data

Jan. 27, 1992 [DE] Germany .................. 42 02 125.1

[51] Int. Cl.⁶ .................... F16K 51/02; G01N 37/00
[52] U.S. Cl. .................... 73/864.84; 250/288
[58] Field of Search .................. 73/864.81–864.87; 252/288, 288 A

[56] References Cited

U.S. PATENT DOCUMENTS

| | | | |
|---|---|---|---|
| 2,702,479 | 2/1955 | Black et al. | 250/288 X |
| 2,721,270 | 10/1955 | Bennett | 250/288 |
| 2,769,912 | 11/1956 | Lupfer et al. | 250/288 |
| 3,014,128 | 12/1961 | Taubert | 73/864,84 X |
| 3,187,179 | 6/1965 | Craig et al. | 250/288 |
| 3,458,699 | 7/1969 | Padrta | 250/288 |
| 3,471,692 | 10/1969 | Llewellyn et al. | 250/288 A |
| 3,594,574 | 7/1971 | Morgan et al. | |
| 4,213,326 | 7/1980 | Brodasky | 73/23.37 |
| 4,399,690 | 8/1983 | Fruzzetti | 73/40.7 |
| 4,590,371 | 5/1986 | Ottley | 250/289 |
| 4,672,203 | 6/1987 | Holkebuer | 250/289 |
| 5,197,712 | 3/1993 | Engelhardt | 251/335.3 |

FOREIGN PATENT DOCUMENTS 27693 3/1977 Japan ................ 250/288

OTHER PUBLICATIONS

Vacuum Technology, Alexander Roth, (1976), pp. 340, 426–427, *Elsevier Science Publishers B.V., 1976, 1982, 1990.*

Ultrahigh Vacuum Practice, G. F. Weston, (1985), PP. 23–25 *Butterworth & Co., Ltd.*

Primary Examiner—Thomas P. Noland
Attorney, Agent, or Firm—Cesari and McKenna

[57] ABSTRACT

An ultra-high vacuum valve for the admission of substance mixtures into an analytical measuring instrument limits the flow path of the substances to as small a flow chamber as possible with controllable chamber wall adsorption properties. The elastic wall sections necessary for movement of the valve piston are located in a mechanical chamber separated from the flow chamber by a wall. The mechanical chamber is evacuated by means of a separate vacuum duct and a seal is used to seal the valve piston where it passes through the wall.

20 Claims, 1 Drawing Sheet

INLET VALVE FOR A HIGH-VACUUM ANALYZER WITH BYPASS EVACUATION

FIELD OF THE INVENTION

The invention concerns an ultra-high vacuum valve for the admission of substance mixtures into an analytical measuring instrument, the analytically active sensor of which is in a high vacuum, in particular, a mass spectrometer.

BACKGROUND OF THE INVENTION

Highly sensitive analytical instruments with measuring sensors in a high vacuum (such as mass spectrometers) are nowadays able to measure concentrations of trace substances down to 1 ppb (one billionth of the weight) at a total gas inflow of only 10 nanoliters per second (corresponding to approximately 10 nanograms per second). These are trace substance flows of only $10^{-17}$ grams per second, corresponding to $10^5$ molecules per second for a substance with a molecular weight of 60 Daltons (one Dalton is equal to one atomic mass unit).

If a surface coming into contact with the inflowing gas is active in adsorbing one of the trace substances to be analyzed, it can very easily completely prevent the flow of this trace substance into the measuring instrument for a long time. In comparison, a single square millimeter of an active surface can adsorb 1 nanogram ($10^{-9}$ grams) of a substance with a molecular weight of approximately 300 Daltons before it is saturated with a monomolecular layer.

Chromatographic capillary columns, which have an excellent low level of adsorption, are nowadays almost exclusively used for inflow of the substance to the mass spectrometer. The columns are heated in order to keep the substances vaporous and avoid condensation. High-temperature-resistant chromatographic phases capable of being heated up to 400° C. are already known.

It is advantageous to keep analytical high-vacuum instruments, such as mass spectrometers, permanently at a high vacuum in order not to have to constantly reproduce clean measuring conditions by means of lengthy baking processes when the measuring systems are returned to use. Accordingly, high-vacuum analyzers, which do not operate with permanently connected capillary columns and are kept at a vacuum round the clock by active pumping, require an ultrahigh vacuum valve (UHV valve) in order to admit substances for testing. This particularly concerns mass spectrometers for mobile use evacuated with ion getter pumps and transported at a vacuum in a sealed state.

The valve used with such systems must be ultrahigh-vacuum-tight and able to withstand baking periods up to 400° C. without any limitation of function. The normal operational temperature during opening times is 250° C. in order to avoid condensation of the substances admitted.

Inlet valves for substance mixtures to be analytically examined for trace materials must meet the requirements stated above concerning freedom of adsorption. On the other hand, inlet valves need to have elastic wall pieces, such as metal membranes or metal bellows, in order to be able to move a valve piston into the inlet path by means of an external force.

These elastic wall pieces, however, constitute a problem for surface adsorption because the choice of material for the surface is limited by the elasticity requirements. Since they have to accommodate a motion stroke, they generally have an unfavorably large surface area. In addition, the surface of metal membranes or metal bellows frequently contains rolled-in organic materials. These materials are given a diffusion thrust by each elastic movement and am released in minute traces, thus, a chemical background is constantly present. This behavior cannot be eliminated either by baking or by cleansing surface treatments.

It is the task of the invention to produce a valve in which disruptive adsorption and outgassing into the substance flow entering the analytical instrument are restricted to a minimum.

SUMMARY OF THE INVENTION

In accordance with one embodiment of the invention, the path of the test substances is limited to as small a flow chamber as possible with controllable chamber wall adsorption properties. In order to do this the elastic wall sections necessary for movement of the valve piston are located in a separate mechanical chamber which is evacuated by a separate connection to the vacuum pump. The flow chamber and the mechanical chamber are separated by a wall and the valve piston is sealed where it passes through this wall.

DETAILED DESCRIPTION OF THE PREFERRED EMBODIMENT

Figure 1:
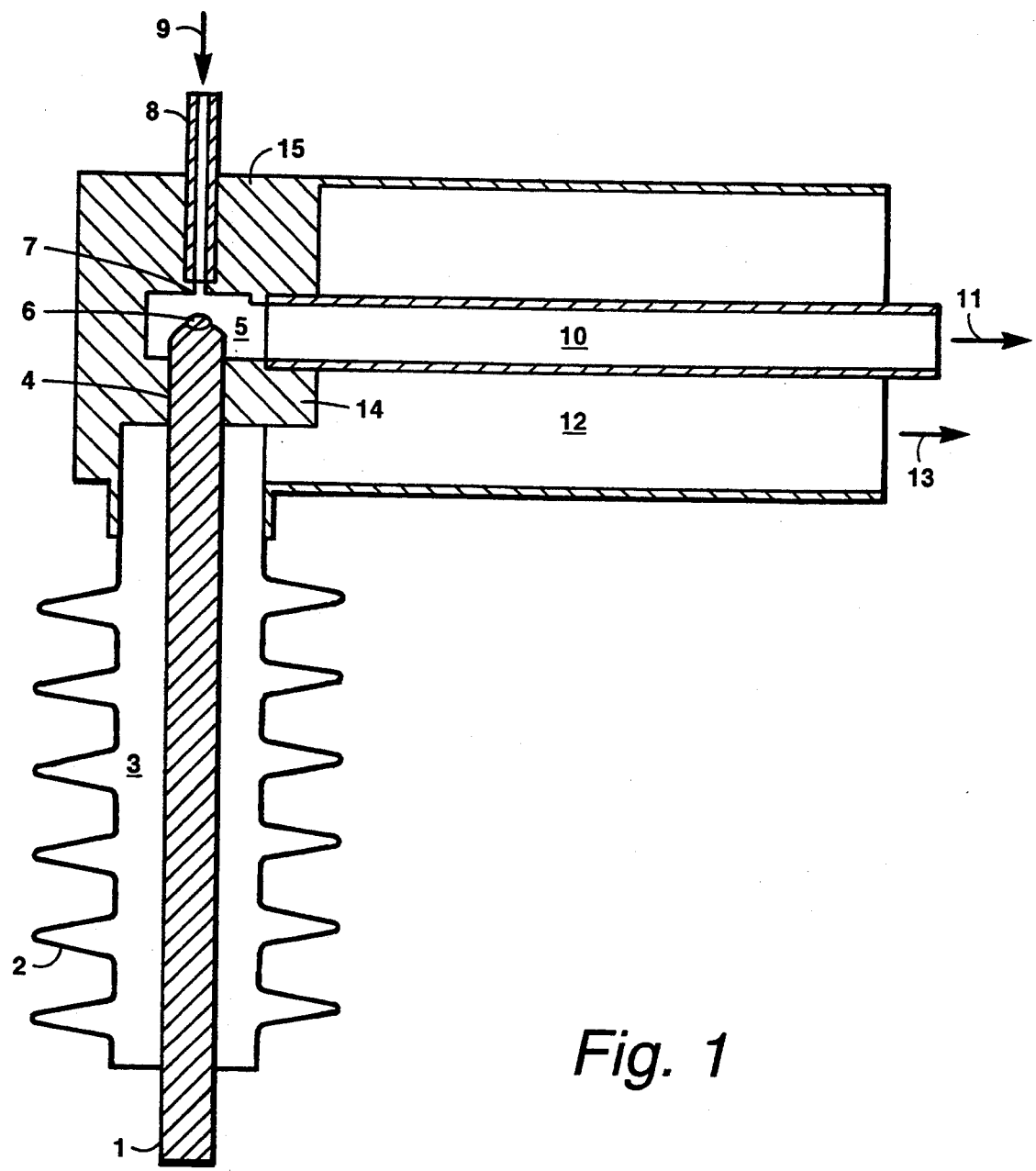
FIG. 1 is a cross-sectional diagram of an ultra-high vacuum valve constructed in accordance with the principles of the invention.

FIG. 1 illustrates a preferred embodiment of the invention in which the inventive valve body (15) is comprised of two chambers (3) and (5). The flow chamber (5) in the valve for the flow of the gas mixture to be analyzed is separated by a wall (14) from the mechanical chamber (3) containing the elastic wall element (2). The mechanical chamber (3) with the elastic wall element (2) is evacuated by the vacuum pump of the UHV analyzer (not shown), but in such a way that the impurities released from the elastic wall piece (2) are able to reach the vacuum pump of the UHV instrument directly, circumventing the sensor chamber of the UHV instrument critical for the analysis. The flow chamber (5) can then be made of conventional materials, such as stainless steel, the surface of which can be inactivated by means of known methods, such as electropolishing or silylation.

The head (6) of the valve piston (1) in the flow chamber (5), which causes the valve to close by being pressed against the valve seat (7), is of particular importance. A piston head manufactured from metal is slightly deformed each time the valve closes due to inelastic sliding processes in the crystalline structure of the metal. This deformation exposes fresh points of the metal surface after opening which are generally extremely adsorptive.

A preferred embodiment of tile invention therefore provides for a sphere (6) made of extremely hard and inert material with little brittleness which shows no inelastic deformation. Particularly suitable materials are diamond, boron carbide, sapphire or silicon nitride, these materials being very inert both chemically and in terms of surface properties. The valve seat (7) is deformed into the shape of the sphere (6) during the first few closures of the valve and thereafter shows no further inelastic deformation upon further closing of the valve. In the preferred embodiment, the valve seat (7) is foraged integrally with the valve body (15) and may therefor be comprised of the same material as the valve body (15), for example, high-quality stainless steel. Alternatively, the valve seat (7) may be formed of a different material from the valve body.

A further possible means of separating the mechanical chamber (3) from the flow chamber (5) is to provide the valve piston (1) with a thicker part or additional valve member (not shown) located below the sealing sphere which additional valve member mates with a rear sealing face in wall (14) when the valve (6, 7) is opened. This rear sealing face does not need to satisfy the strict UHV requirements concerning tightness because the mechanical chamber (3) is evacuated to a vacuum near the vacuum in the flow chamber (5). In practice, however, this type of seal has shown itself to be only a second-best solution to the problem since undesirable adsorption and desorption processes have been repeatedly observed at this seal seat.

In a preferred embodiment of the invention as shown in FIG. 1, a cylindrical valve piston (1) of hardened material such as stainless steel, can be moved along its longitudinal axis as permitted by the elastic metal bellows (2). The mechanical chamber (3), which makes possible movement of the valve piston (1), is separated from the flow chamber (5) by a diffusion gap (4) with a very low conductance (width approx. 0.05 ram), permitting only an extremely low substance flow under the prevailing vacuum conditions of approximately $10^{-4}$ Pa in the bellows chamber (3) and $10^{-3}$ Pa in the flow chamber (5). The valve head consists of a silicon nitride sphere (6) which can be pressed into the stainless steel valve seat (7). The inlet tube (8) for the substance inflow (9) and outlet tube (10) leading to the ion source (path direction 11 ) are made of inactivated quartz glass.

The bellows chamber (3) is pumped out via the bypass pipe (12) in the path direction of the vacuum pump (13) in order to maintain the favorable pressure difference via the diffusion gap (4).

The diffusion gap (4) was selected as a sealant even though it is not completely vacuum tight. Sliding seals of high-temperature-resistant organic materials (e.g. polyimide) can also be used without having to fear the piston seizing with frequent movements. On the other hand, friction processes in a vacuum always involve a release of adsorbed substances. In addition, organic materials adsorb traces of substances particularly easily by means of dissolving processes. Both processes are avoided by a diffusion gap.

What is claimed is:

1. A valve for admitting a flow of a gas mixture into a high-vacuum analyzer for analysis, the valve comprising:
   a valve body having first chamber connected to the high-vacuum analyzer and a second chamber therein separated from the first chamber by a wall;
   a mechanically-operated valve located in the first chamber for controlling the flow of the gas mixture to the high-vacuum analyzer, the valve comprising a mechanical actuator which passes through the second chamber and the wall and moves to open and close the valve;
   a flexible vacuum-tight connection between the valve actuator and the second chamber where the valve actuator passes out of the second chamber;
   a seal sealing the valve actuator where it passes through the wall, the seal substantially reducing the flow of the gas mixture between the first chamber to the second chamber; and
   means for evacuating the second chamber.

2. A valve according to claim 1 wherein the seal comprises a fine diffusion gap between the wall and the valve actuator.

3. A valve according to claim 1 wherein the seal comprises a sliding seal through which the valve actuator can move.

4. A valve according to claim 1 wherein the seal comprises a valve mechanism located on the mechanical actuator, which valve mechanism seats against the wall when the valve is opened by the actuator.

5. A valve according to any one of the preceding claims wherein the valve comprises a valve seat and a sphere comprised of a hard, smooth, non-brittle and non-adsorptive material, which sphere cooperates with the valve seat to control the flow of gas into the first chamber.

6. A valve according to claim 5 wherein the sphere is comprised of a material selected from the group consisting of diamond, boron carbide, sapphire and silicon nitride.

7. A valve according to any one of claims 1-4 further comprising an inlet tube for directing a flow of gas to the first chamber, and an outlet tube connecting the first chamber to the high-vacuum analyzer.

8. A valve according to claim 7 wherein the inlet tube and the outlet tube are comprised of a material selected from the group consisting of inactivated glass and quartz glass.

9. A valve for admitting a flow of a gas mixture for analysis into a high-vacuum analyzer, the valve comprising:
   a valve body having first chamber connected to the high-vacuum analyzer and a second chamber therein separated from the first chamber by a wall;
   a gas inlet tube connected to the valve body for delivering the flow of the gas mixture to the first chamber;
   a mechanically-operated valve piston, the valve piston cooperating with the gas inlet tube to control the flow of the gas mixture from the gas inlet tube to the first chamber, the valve piston passing through the second chamber and the wall;
   an elastically flexible vacuum wall connecting the valve piston to the second chamber at the point where the valve piston passes out of the second chamber to permit mechanical movement of the valve piston;
   a vacuum seal disposed about the valve piston at the point where it passes through the wall, the vacuum seal substantially reducing the flow of the gas mixture from the first chamber to the second chamber; and
   means for evacuating the second chamber.

10. A valve according to claim 9 wherein the vacuum seal comprises a fine diffusion gap between the wall and the valve piston.

11. A valve according to claim 9 wherein the vacuum seal comprises a sliding seal through which the valve piston can move.

12. A valve according to claim 9 wherein the vacuum seal comprises a valve mechanism located on the valve piston, which valve mechanism seats against the wall when the piston retracts to open the valve.

13. A valve according to any one of claims 9-12 wherein the valve comprises a valve seat and a sphere comprised of a hard, smooth, non-brittle and non-adsorptive material, which sphere cooperates with the valve seat to control the flow of gas into the first chamber.

14. A valve according to claim 13 wherein the sphere is comprised of a material selected from the group consisting of diamond, boron carbide, sapphire and silicon nitride.

15. A valve according to claim 9 further comprising a gas outlet tube connecting the first chamber to the high-vacuum analyzer.

16. A valve according to claim 15 wherein the inlet tube and the outlet tube are comprised of a material selected from the group consisting of inactivated glass and quartz glass.

17. A valve for admitting a flow of a gas mixture for analysis into an ion source chamber of an analytical mass spectrometer, the valve comprising:
- a valve body having first chamber connected to the ion source chamber and a second chamber therein separated from the first chamber by a wall;
- a gas inlet tube connected to the valve body for delivering the flow of the gas mixture to the first chamber;
- a valve seat located at the end of the gas inlet tube;
- a cylindrical, sliding valve piston, the valve piston cooperating with the valve seat to control the flow of the gas mixture from the gas inlet tube into the first chamber, the valve piston passing from outside the valve body through the second chamber and the wall into the first chamber;
- a flexible vacuum bellows connecting the valve piston to the second chamber at the point where the valve piston passes out of the second chamber to permit the valve piston to slide;
- a vacuum seal disposed about the valve piston at the point where it passes through the wall, the vacuum seal substantially reducing the flow of the gas mixture from the first chamber to the second chamber; and
- means for connecting the second chamber to a vacuum source to evacuate the second chamber.

18. A valve according to claim 17 wherein the valve piston passes through a hole in the wall and the clearance between the valve piston and the wall is sufficiently small that a fine diffusion gap is formed between the wall and the valve piston.

19. A valve according to claim 17 wherein the vacuum seal comprises a sliding seal through which the valve piston can move.

20. A valve according to claim 17 wherein the valve piston has an end which cooperates with the valve seat to form the valve and the vacuum seal comprises a second valve seat located on the valve piston and spaced from the valve piston end, which second valve seat seats against the wall when the piston retracts to open the valve.

* * * * *